United States Patent [19]

Sinnett

[11] Patent Number: 5,334,163

[45] Date of Patent: Aug. 2, 1994

[54] APPARATUS FOR PREPARING AND ADMINISTERING A DOSE OF A FLUID MIXTURE FOR INJECTION INTO BODY TISSUE

[76] Inventor: Kevin B. Sinnett, W273 S8555 Hill View Dr., Mukwonago, Wis. 53149

[21] Appl. No.: 945,684

[22] Filed: Sep. 16, 1992

[51] Int. Cl.⁵ .......................................... A61M 5/315
[52] U.S. Cl. ..................................... 604/236; 604/4;
137/625.47
[58] Field of Search ..................................... 604/81–83,
604/89–93, 181–188, 207, 232–238, 246,
259–260, 298, 300, 221–222, 201–201;
137/625.47

[56] References Cited

U.S. PATENT DOCUMENTS

| | | | |
|---|---|---|---|
| 2,845,067 | 7/1958 | Gabriel | 604/148 |
| 3,344,785 | 10/1967 | Hamilton | 604/4 |
| 4,112,945 | 9/1978 | Helixon et al. | 604/220 |
| 4,306,554 | 12/1981 | Schwartz et al. | 604/87 |
| 4,967,797 | 11/1990 | Manska | 137/625.47 |
| 4,979,942 | 12/1990 | Wolf et al. | |
| 5,019,037 | 5/1991 | Wang et al. | |
| 5,066,276 | 11/1991 | Wang | |
| 5,288,290 | 2/1994 | Brody | 604/32 |

Primary Examiner—C. Fred Rosenbaum
Assistant Examiner—V. Alexander
Attorney, Agent, or Firm—Godfrey & Kahn

[57] ABSTRACT

An apparatus (10) for preparing and administering a dose of a fluid mixture for injection into body tissue includes a syringe assembly (20), a valve (30), a vessel (60) containing a pressurized fluid, and an infusion cannula (70). The valve (30) has a first passageway (98), a second passageway (99), a third passageway (100), and a fluid flow director (96). The fluid flow director (96) selectively directs fluid flow between any two of the passageways, and simultaneously shuts off flow to the third. The first passageway (98) is connected to a fluid receiving reservoir with the syringe assembly (20), the second passageway is removably connected to the infusion cannula (70), and the third passageway (100) is connected to the vessel (60). By use of the fluid flow director (96), a predetermined volume of the pressurized fluid is directed into the fluid receiving reservoir within the syringe assembly (20), through the third passageway (100) and a predetermined volume of air is drawn into the fluid receiving reservoir through the second passageway (99) when the cannula (20) is removed from the fluid mixture. The cannula (70) is then attached for injection of the fluid mixture into the desired body tissue.

18 Claims, 4 Drawing Sheets

APPARATUS FOR PREPARING AND ADMINISTERING A DOSE OF A FLUID MIXTURE FOR INJECTION INTO BODY TISSUE

FIELD OF THE INVENTION

The present invention relates generally to a fluid injection apparatus, and more particularly, to a disposable apparatus for preparing a single dose of a fluid mixture for injection into body tissue, such as an eye, during a medical procedure, such as a pneumatic retinopexy or to provide tamponade during post-vitrectomy for purposes of reattaching the retina.

BACKGROUND OF THE INVENTION

A syringe has been used since the early part of the twentieth century to inject air into the vitreous cavity of an eye to correct a retinal detachment of the eye. In a procedure known as a "pneumatic retinopexy," the injected air gives tamponade to a retinal hole in the eye and holds the retina of the eye in a position of reattachment until the adhesive modality between the retina and the pigment epithelium of the eye has achieved adequate strength. Such injection of air as a medical procedure is referred to as "insufflation," and for the case of injection into the vitreous cavity, "intravitreal insufflation." The injection of air into the eye may be performed for other medical procedures as well. For example, when the vitreous of an eye is surgically removed, during vitrectomy, the air may be used to provide full tamponade following such procedure, also for purposes of reattaching the retina. Some surgeons have used air for total ocular fluid replacement even without retinal detachment, with good results and apparently no recognized complications.

The use of air for intravitreal insufflation in a pneumatic retinopexy or after vitrectomy has the advantage of no known toxicity. However, a major drawback associated with the use of air is that it may be absorbed by body tissue more rapidly than desired, that is, before a firm pigment epithelium-retinal adhesion has formed, thereby limiting its usefulness as an effective tamponade. However, despite its lack of chemical toxicity, air may have the additional disadvantage of causing physical problems within the eye. For example, if a patient is being operated under general anesthesia, nitrous oxide should be discontinued ten minutes prior to the air insufflation to allow clearance of the nitrous oxide from the body. The discontinuance of nitrous oxide is required because it is a soluble gas and rapidly moves from the venous blood into the injected intravitreal bubble of gas, thereby causing rapid expansion of the bubble with a simultaneous rise in intraocular pressure. However, the nitrous oxide leaves the bubble just as rapidly, so that if it has not been discontinued, the intravitreal bubble rapidly shrinks when the anesthesia is discontinued, giving a lesser degree of insufflation than desired.

To alleviate the problem of air absorption into the body, a fluid having a slower rate of tissue absorption is desirable. Gases which may be used as an effective substitute for air in ophthalmic procedures are sulfur hexafluoride ($SF_6$) or perfluoropropane ($C_3F_8$). Sulfur hexafluoride is a chemically inert gas which has not proved to be toxic, is highly lipid soluble, and has a very low water solubility. For these reasons, sulfur hexafluoride remains in body tissue pockets for about twice as long as air. As may be appreciated, the duration a sulfur hexafluoride bubble remains within the intraocular region of the eye depends on the variables of the initial concentration and the volume injected. The greater the amount of the either of the variables, the more the bubble of sulfur hexafluoride expands, thereby maintaining its presence as a therapeutic tamponade over a longer period of time. However, when pure sulfur mexafluoride is used in a tissue pocket, such as a vitreous cavity, its volume expands for about two days, which causes substantial increases in intraocular pressure. Therefore, the vitreous cavity should never be completely filled with pure sulfur hexafluoride.

Intraocular pressure elevation resulting from sulfur hexafluoride volume expansion is usually avoided if the vitreous cavity is not filled with more than 40% pure sulfur hexafluoride. An alternative to such a procedure is to inject a precisely measured mixture of sulfur hexafluoride and air in such a ratio which corresponds to the ratio that would develop spontaneously in the eye if the vitreous cavity were filled with pure sulfur hexafluoride to not more than 40% of the volume of the eye, as in the aforementioned procedure. In this regard, it has been discovered that for clinical purposes, a mixture composed of 40% sulfur hexafluoride and 60% air will not expand. Accordingly, it has been found that such a fluid mixture can be used to fill the entire vitreous cavity during an ophthalmic procedure without resulting in a substantial increase in intraocular pressure. Therefore, there exists a need for an apparatus to efficiently and accurately prepare a fluid mixture, such as a mixture consisting of 40% sulfur hexafluoride and 60% air, for injection into body tissue, such as an eye, during a medical procedure such as a pneumatic retinopexy.

While widely diverse in construction and operation, prior art apparatuses and methods for preparing a fluid mixture in a syringe for injection into body tissue, such as an eye, are replete with deficiencies and shortcomings which have detracted from their usefulness. Foremost among the deficiencies of the previously employed apparatuses is their apparent inability to accurately and efficiently prepare a fluid mixture in a syringe for injection into the intraocular region of the eye. Previously, to prepare a fluid mixture consisting of 40% sulfur hexafluoride and 60% air, a syringe was first connected to a pressurized lab cylinder filled with air and the syringe was filled to a predetermined volume. The syringe was then disconnected and connected to a pressurized lab cylinder filled with sulfur hexafluoride, and the syringe was filled to a predetermined volume. As may be appreciated, such a procedure is awkward and time consuming, and requires a number of persons to accomplish.

Another deficiency of the previously employed apparatuses is the apparent unavailability of a commercially produced apparatus which conveniently fills a syringe with either an air or a fluid mixture. Typically, doctors and surgeons have constructed makeshift apparatuses for filling a syringe with air or fluid. Although such apparatuses may have accomplished their purposes with varying degrees of success, they are inaccurate, and in some cases unsafe. More particularly, these makeshift apparatuses may permit the fluid mixture to leak from a syringe during the preparation of the fluid mixture, thereby producing inaccurate measurements which affect intraocular eye pressure. Safety also may be compromised if regulating valves are not employed with such makeshift apparatuses, as it is common for an end of a syringe to blow out, thereby introducing flying debris and jeopardizing the safety of all personnel present.

Still another deficiency of the prior art devices is the inordinate amount of care required to ensure a sterile transfer of air or gas to the syringe. As may be appreciated, to prepare the syringe with a fluid mixture, the syringe is connected to a pressurized air source and then disconnected, and then connected to a pressurized source of gas, such as sulfur hexafluoride, and then disconnected. The sterility of the syringe is thereby placed at risk because of the multiple steps which place the syringe in contact with multiple foreign objects before the bubble is injected into the intraocular region of the eye.

Yet another deficiency attendant with previously employed devices is their relative unpredictability in operation resulting from their makeshift design. Typically, these devices were produced by doctors or surgeons from spare parts which may not have been designed for such use. Accordingly, there is an increased likelihood that these apparatuses will fail or otherwise malfunction during operation.

Still another deficiency of the previously employed devices is their apparent inability to reduce waste of compressed air or compressed gas. As previously described, compressed air and compressed gas typically have leaked from the laboratory cylinders or the syringe during the syringe preparation process. This, of course, wastes resources and causes an increase in attendant medical costs.

Accordingly, a need has arisen for an apparatus which quickly, effectively and accurately prepares a single dose of fluid for injection into body tissue, and which is disposable and convenient, thereby rendering such an apparatus particularly suitable for use in a surgical operating room, or in a medical doctor's office for out-patient medical procedures.

SUMMARY OF THE INVENTION

In accordance with the present invention, an apparatus for preparing a fluid mixture for injection into body tissue during a medical procedure includes a syringe having a hollow barrel with a plunger which travels within the barrel to regulate fluid flow therethrough. The barrel is disposed in fluid communication with either a pressurized source of fluid or ambient air by means of a stopcock, and includes indicia for measuring a volume of fluid. The stopcock has a first passageway, a second passageway, a third passageway, and a fluid flow director which selectively directs fluid between predetermined passageways during use of the apparatus. The stopcock is mounted on the barrel such that the first passageway is placed in fluid communication with the barrel. A first filter assembly is mounted on the stopcock in fluid flowing relation to the third passageway, and an adapter assembly is then mounted on the first fluid filter. A source of pressurized fluid is mounted on the adapter assembly, and when mounted thereon, the fluid is permitted to flow from the fluid source to the barrel through the first fluid filter. A second fluid filter is removably mounted on the stopcock in fluid flowing relation to the passageway, and a hollow infusion cannula is removably mounted to the second fluid filter.

It is an object of the present invention to provide an improved apparatus for preparing a fluid mixture for injection into body tissue, such as an eye, during a medical procedure, such as during pneumatic retinopexy.

Another object of the present invention is to provide an apparatus which quickly, efficiently, and accurately prepares a gas-air mixture within a syringe in a predetermined ratio.

Another object of the present invention is to provide an apparatus which is disposable after a single use.

Another object of the present invention is to provide an apparatus which is compact in design and convenient in use, and which is particularly suitable for use in either a surgical operating room or a medical doctor's office.

Another object of the present invention is to provide an apparatus which is of relatively moderate cost to purchase.

Another object of the present invention is to provide an apparatus which is characterized by ease of employment and simplicity of construction.

Another object of the present invention is to provide an apparatus which is commercially available to all medical personnel, thereby eliminating the need for medical personnel to construct makeshift devices for preparing a fluid mixture in a syringe.

Another object of the present invention is provide an apparatus which substantially eliminates the waste of pressurized gas or pressurized air during the use.

Another object of the present invention is to provide an apparatus which substantially eliminates the risk of contamination of a syringe during the preparation of a fluid mixture therein.

Additional objects and advantages of the present invention are to provide improved elements and arrangements thereof in an apparatus for the purposes described which is dependable, economical, disposable and fully effective in accompanying its intended purpose.

Further objects, features, and advantages of the invention will be apparent from the following detailed description taken in conjunction with the accompanying drawings.

DETAILED DESCRIPTION OF THE PREFERRED EMBODIMENT

Figure 1:
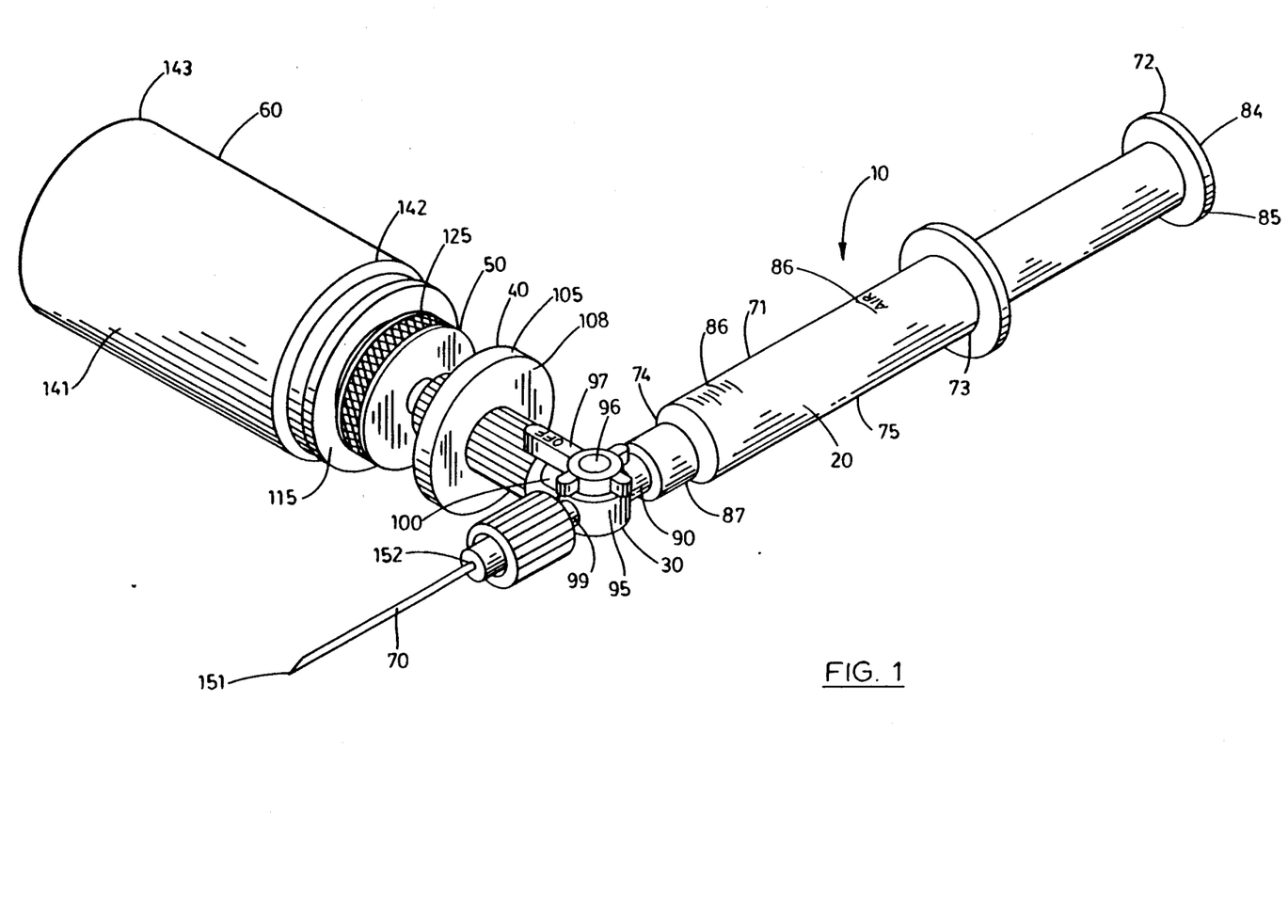
FIG. 1 is a perspective view of the apparatus of the present invention which prepares a fluid mixture for injection into body tissue, the apparatus being shown in an arrangement just prior to injection.
Figure 2:
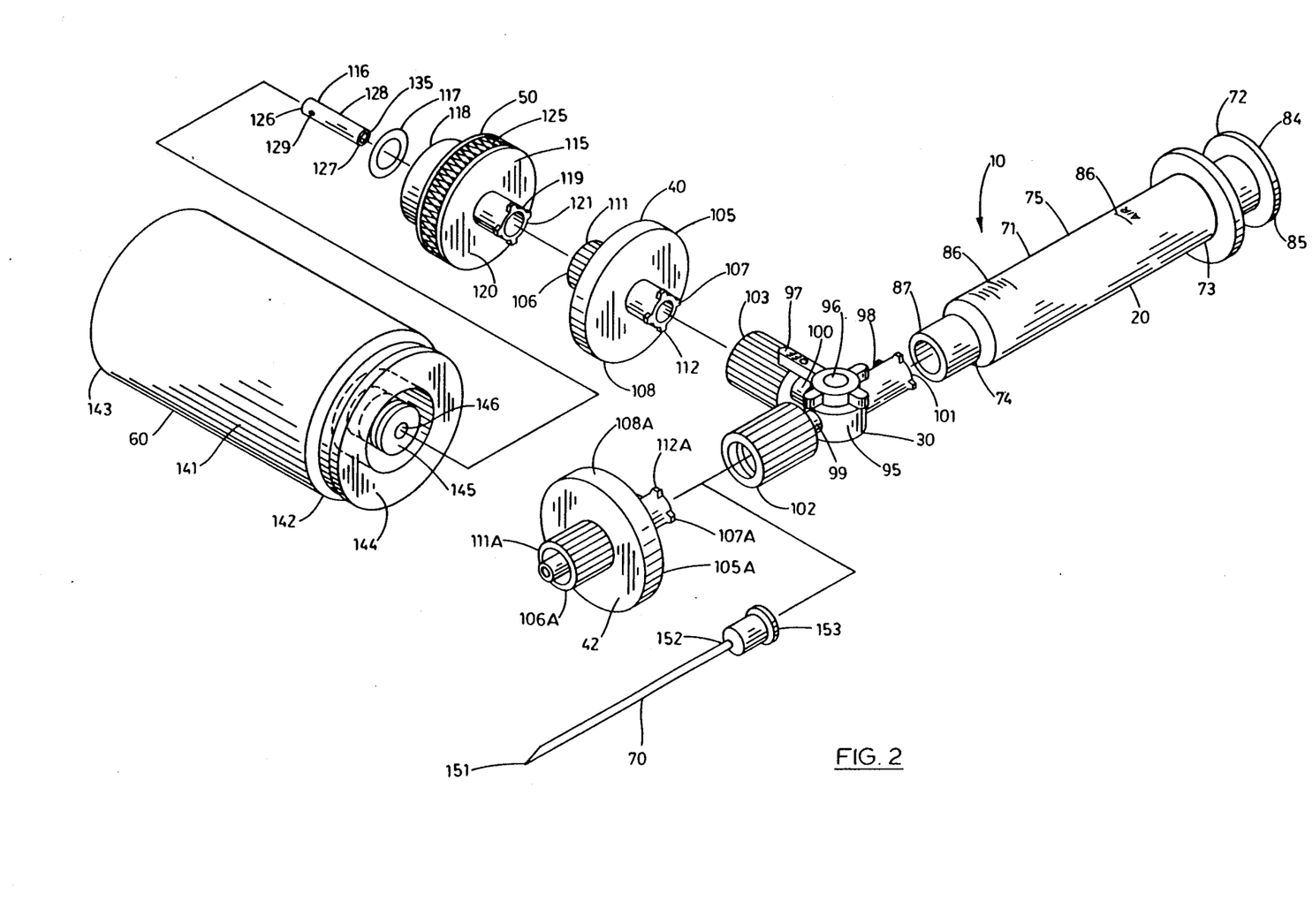
FIG. 2 is an exploded, perspective view of the apparatus of the present invention.

With reference to the drawings, an apparatus for preparing and administering a dose of a fluid mixture for injection into body tissue in accordance with the present invention is shown generally at 10 in FIGS. 1 and 2. The apparatus 10 is sized so as to be hand-held, and is disposable after a single use. The apparatus 10 comprises a syringe assembly 20, a valve 30 for regulating fluid flow, a first fluid filter 40, a second fluid filter 42, an adapter assembly 50, a vessel 60 containing a pressurized fluid, and an infusion cannula 70. FIG. 1 shows these and other parts in an assembled arrangement, and in an operational configuration just prior to injection of a dose of a fluid fixture into body tissue, such as an eye. FIG. 2 shows these and other parts in an exploded perspective view to highlight the relationship and assembly of the individual parts with respect to each other.

The syringe assembly 20 includes a hollow, axially-directed, cylindrically-shaped barrel 71 and a plunger 72. The barrel 71 includes a first end 73 and a second end 74. The syringe barrel 71 has an exterior surface 75 which defines an outer barrel diametral dimension, and an interior surface (not shown) which defines an inner diametral dimension and a fluid receiving reservoir (not shown) having a predetermined volume. The plunger 72 includes a first end (not shown) which is adapted to be received by the first end 73 of the syringe barrel 71, and an axially opposed second end 84 which has formed thereon an annular grip 85. The plunger 72 is conformably dimensioned to be axially slidable within the fluid receiving reservoir of the syringe barrel 71. The first end of the plunger 72 forms a seal against the interior surface of the barrel 71 such that axial travel of the plunger 72 within the barrel 71 creates a fluid pumping action. Accordingly, when the plunger 72 is disposed therein, and when the plunger is pulled in a direction toward the first syringe barrel end 73, the plunger 72 causes a pumping action within the fluid receiving reservoir, between the first plunger end and the second syringe barrel end 74, in a direction toward the first syringe barrel end 73. Travel of the plunger 72 toward the first end 73 therefore draws fluid into the fluid receiving reservoirs of the barrel 71. Moreover, when the plunger 72 is pushed toward the second syringe barrel end 74, the plunger 72 causes a pumping action within the fluid receiving reservoir, between the first plunger end and the second syringe barrel end 74, in a direction toward the second syringe barrel end 74. Travel of the plunger 72 toward the second end 74 therefore forces fluid from the fluid receiving reservoir of the barrel 71. The plunger 72 thereby serves to regulate fluid flow within the fluid receiving reservoir of the syringe barrel 71. The barrel 71 is transparent or translucent so as to be able to view the position of the plunger 72 within the fluid receiving reservoir. The exterior surface 75 of the syringe barrel 71 includes a volume indicating means 86 made integral thereon, such as, for example, a plurality of reference lines as illustrated in FIGS. 1-5. The volume indicating means 86 permits medical personnel to prepare a precise fluid mixture within the fluid receiving reservoir of the syringe barrel 71 of a fluid mixture by a viewing of the relative plunger position against the volume indicating means 86.

The second end 74 of the syringe barrel 71 has formed integral therewith a removably connectable male coupling 87. A removably connectable coupling well suited for use as the male coupling 87 in the present invention is a LUER-LOK ® fitting, manufactured by Becton, Dickenson and Company of Rutherford, N.J. LUER-LOK ® fittings are widely known, and are typically incorporated into medical devices as removably connectable fittings. LUER-LOK ® fittings permit two discrete parts of a medical apparatus to be selectively connected or disconnected in fluid communication, one to the other. As should be understood, a connection formed by two LUER-LOK ® fittings includes a male LUER-LOK ® fitting such as the coupling 87, illustrated in FIG. 2, and a female LUER-LOK ® fitting.

The syringe barrel 71 of the present invention may be manufactured to define a fluid receiving reservoir having any desired predetermined volume. In this regard, individual fluid receiving reservoirs having volumes of either 5 cubic centimeters or 30 cubic centimeters are particularly useful in ophthalmic medical procedures. For example, an apparatus 10 of the present invention having a syringe barrel 71 which includes a fluid receiving volume of 30 cubic centimeters is useful when employed in an ophthalmic surgical procedure such as a pneumatic retinopexy. The 30 cubic centimeter volume of fluid is particularly well suited to sufficiently insufflate the intraocular region of an eye with a fluid mixture to tamponade the sensory retina of the eye to the pigment epithelium of the eye throughout a therapeutic time period. On the other hand, an apparatus 10 of the present invention having a syringe barrel 71 which includes a fluid receiving reservoir of 5 cubic centimeters is particularly useful for "out-patient" or "post-operative" medical procedures. In a typical "post-operative" use of the apparatus 10, a medical doctor may insufflate an eye to a predetermined intraocular pressure to maintain effective therapeutic tamponade of the sensory retina to the pigment epithelium. Such a procedure would be necessary, for example, if a previously injected fluid mixture had been injected into the intraocular region of the eye and had been absorbed by body tissue more rapidly than anticipated.

Figures 3, 4:
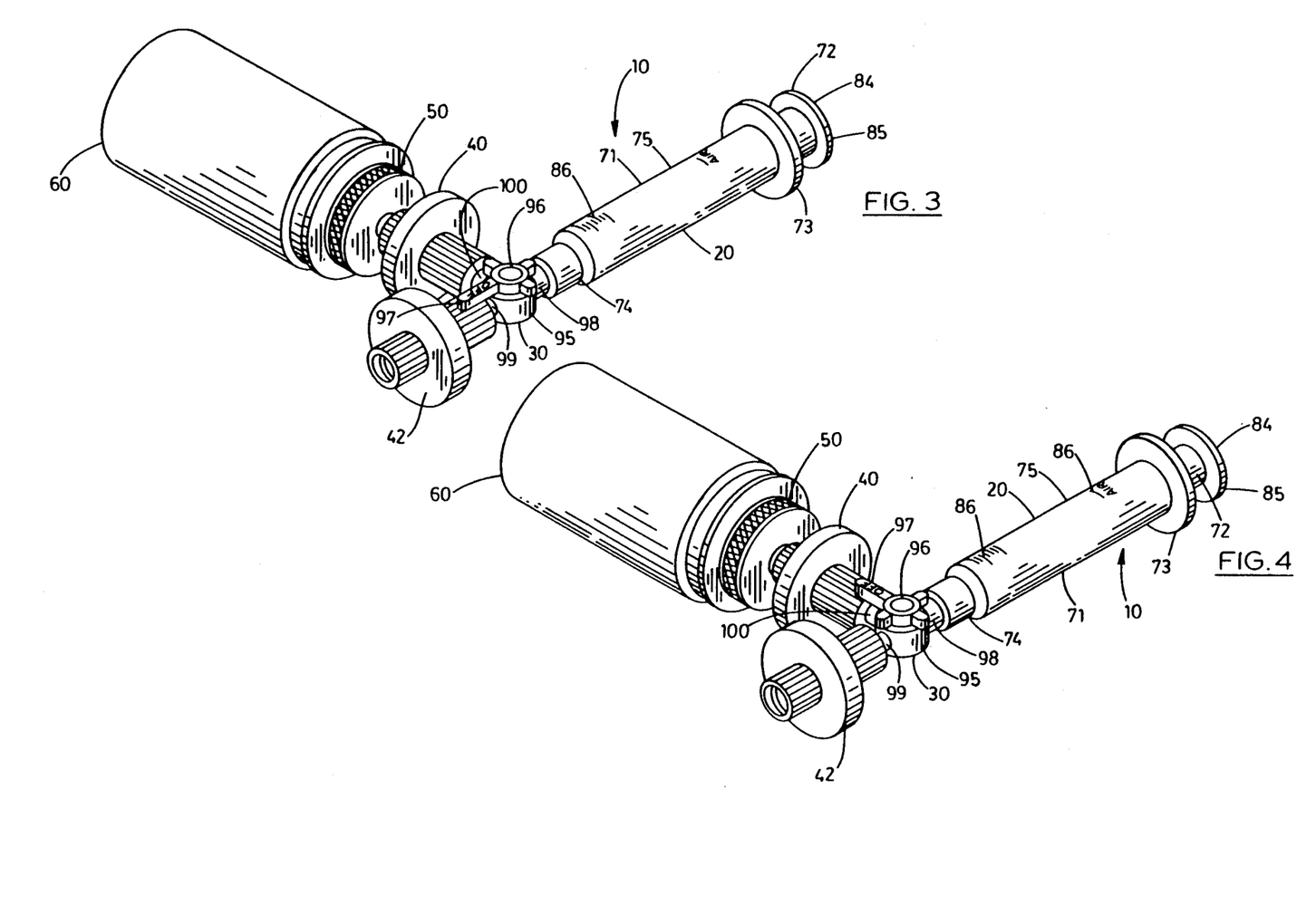
FIG. 3 is a perspective view of the apparatus of the present invention, and wherein the fluid flow director is located in a first position.
FIG. 4 is a perspective view of the apparatus of the present invention, and wherein the fluid flow director is located in a second position.
Figure 5:
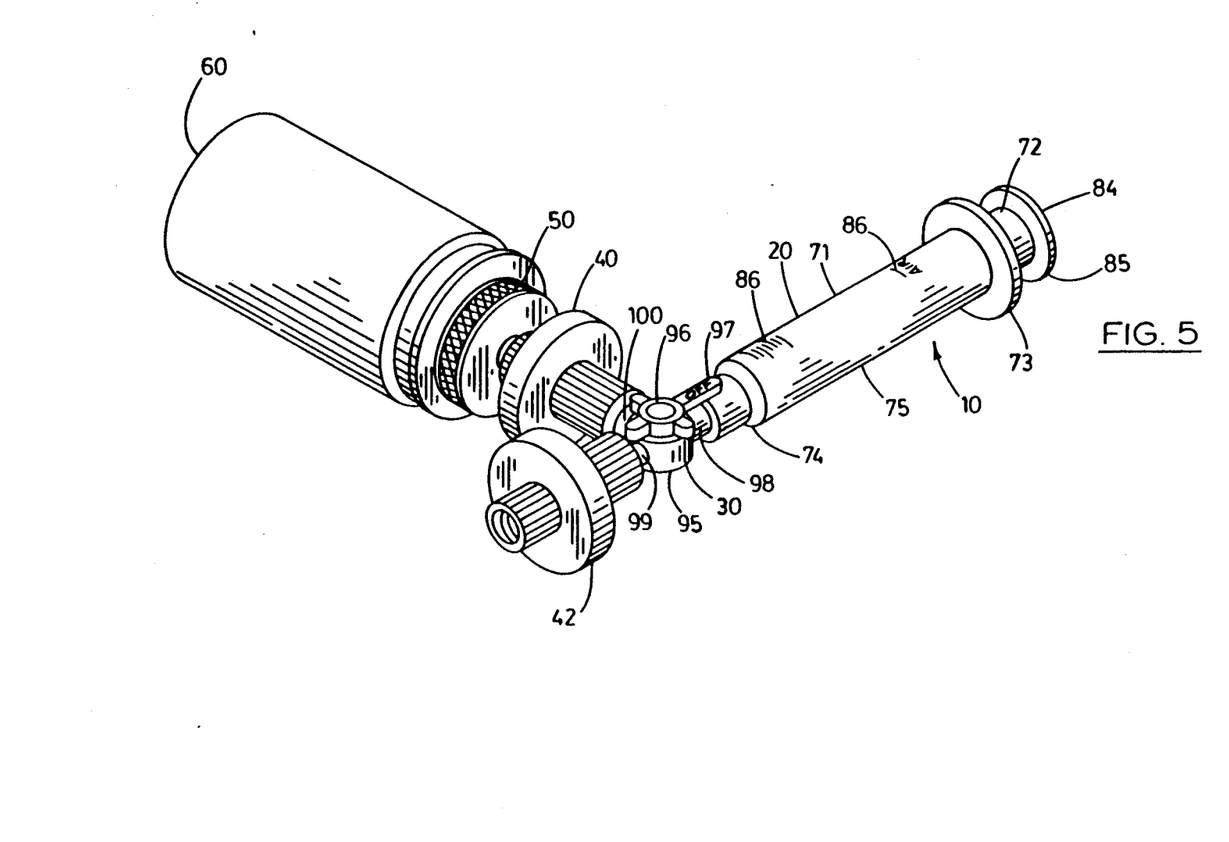
FIG. 5 is a perspective view of the apparatus of the present invention, and wherein the fluid flow director is located in a third position.

The valve 30 is a three-way stopcock which is defined by a main body 95 and includes a fluid flow director 96. The main body 95 defines a first fluid passageway 98, a second fluid passageway 99 and third fluid passageway 100. As best seen by reference to FIG. 2, the first fluid passageway 98 terminates in a female coupling 101 which is removably connectable to the male coupling 87. The second fluid passageway 99 terminates in a male coupling 102, and the third passageway 100 terminates in a male coupling 103. The couplings 101, 102 and 103 are preferably LUER-LOK ® fittings, such as described above. The fluid flow director 96 directs fluid flow between any two of the passageways, the fluid flow director 96 including an indicating lever 97. The indicating lever is marked with the indicium "OFF" to indicate which of the three passageways through which flow is cut off. For example, in FIGS. 1, 2 and 4, the indicating lever 97 has been rotated to a position such that the third passageway 100 is "OFF," so that fluid flow is directed between the first and second passageways 98 and 99. When the indicating lever 97 is positioned such that the second passageway is "OFF," as illustrated in FIG. 3, fluid is permitted to flow within the three-way stopcock main body 95 between the first fluid passageway 98 and the third fluid passageway 100. Further, when the lever assembly 97 is positioned such that the first passageway is "OFF," as illustrated in FIG. 5, fluid is prevented from escaping from the fluid receiving reservoir of the syringe barrel 71. The valve 30 is a conventional stopcock or other single valving means which accomplishes directing of fluid flow such as described above, and as such stopcocks are readily available and understood, description of the internal workings of the valve 30 are not included herein. Operation of the three-way stopcock 95 in the use of the apparatus 10 will be explained in further detail below.

The first fluid filter 40 and the second fluid filter 42 are best detailed in FIG. 2. The first fluid filter includes a main body 105 having a first end 106, an axially opposed second end 107, and a filter membrane mounting portion 108. Mounted within the mounting portion 108 is a hydrophobic-type filter (not shown) which is about 25 millimeters in diameter, and which includes pores dimensioned to be about 0.2 microns. The filter membrane is operable to prevent microbes or other contaminants from entering the fluid receiving reservoir of the syringe barrel 71, through the third passageway 100, during the preparation of a fluid mixture. A supplier of fluid filter assemblies particularly well suited for the present invention is Gelman Sciences, Inc., of Ann Harbor, Mich. A male coupling 111 is mounted on the first end 106 of the first filter main body 105 and a female coupling 112 is mounted on the second end 107. Fluid flowing from the first end 106 toward the second end 107 is therefore conveyed across the filter membrane. The female coupling 112 of the first fluid filter 40 is connected to the male coupling 103 of the third passageway 100. The aforementioned couplings of the first fluid filter 40 are LUER-LOK ® fittings, as described above.

The second fluid filter 42 includes a main body 105A, a first end 106A, a second end 107A, a filter membrane mounting portion 108A, a male coupling 111A, and a female coupling 112A. These parts of the second fluid filter 42 are analogous to the main body 105, the first end 106, the second end 107, the filter membrane mounting portion 108, the male coupling 111, and the female coupling 112 of the first fluid filter 40. Mounted within the mounting portion 108A is a hydrophobic-type filter membrane as described above for the case of the first filter 40. The second filter assembly 42 is operable to prevent microbes or other contaminants from entering the fluid receiving reservoir of the syringe barrel 71, through the second passageway 99, during the preparation of a fluid mixture within the fluid receiving reservoir. The aforementioned couplings of the second fluid filter 42 are LUER-LOK ® fittings, as described above.

As detailed in FIG. 2, the adapter assembly 50 includes a main body 115, a pin 116 and a gasket or O-ring 117. The main body 115 includes a first end 118 and an axially opposed second end 119. The main body 115 is defined by an exterior surface 120 and an interior surface (not shown). The interior surface defines a bore or passageway (not shown) which is oriented in coaxial alignment relative to the first and second ends, 118 and 119, respectively. The passageway permits fluid flow from the first end 118 to the second end 119. Formed on the interior surface of the first end 118 are a plurality of screw threads (not shown) which are dimensioned to screwthreadably receive the source of pressurized fluid 60, described in further detail below. Mounted on, or otherwise made integral with, the second end 119 is a female coupling 121. As should be understood, the adapter assembly 50, by action of the female coupling 121 of the second end 119, and the male coupling 111 of the first end 106 of the first filter assembly main body 105, is adapted to be removably connected on the first fluid filter assembly 40 in fluid communication therewith. The aforementioned couplings 111 and 121 are LUER-LOK ® fittings, as described above. Formed on the exterior surface 120 of the adapter assembly main body 115 is an annular grip 125 which assists a user in the assembly of the apparatus 10. The pin 116 includes a first end 126 and an axially opposed second end 127. The pin 116 is defined by an exterior surface 120 and a interior surface (not shown). A bore 129 is formed perpendicularly through the first end 126 relative to the first and second ends, 126 and 127, respectively. The interior surface of the pin 116 defines a passageway 135 which extends axially within the pin 116 from a predetermined location, which intersects the bore 129, to the second pin end 127. As should be understood, the passageway 135 is disposed in fluid communication with the bore 129. The pin 116 is removably received by the first end 118 to locate the pin 116 within the adapter assembly main body 115. The O-ring 117 is received by the first end 118 of the adapter assembly main body 115. The adapter assembly 50 will be described in further detail below.

The source of pressurized fluid 60 includes a sealed aluminum cylinder or vessel 141 having a fluid reservoir (not shown) which defines a predetermined volume, a first end 142, and a second end 143. The fluid reservoir of the aluminum cylinder is filled with a predetermined volume of a desired fluid such as sulfur hexafluoride gas or perfluoropropane gas. It has been discovered that a fluid reservoir filled with a predetermined volume of either sulfur hexafluoride gas or perfluoropropane gas to about 5 lbs. per square inch is well suited for use in ophthalmic medical procedures. Further, it has been discovered that the pressure within the cylinder fluid reservoir may vary in a range between 4½ lbs. per square inch and 5½ lbs. per square inch without reducing the effectiveness of the apparatus for use in ophthalmic medical procedures. Mounted on, or otherwise made integral with, the first cylinder end 142 is a mounting means 144 which may include a threaded stem 145. As illustrated in FIG. 2, the threaded stem 145 defines a passageway 146 which is disposed in fluid communication with the fluid reservoir of the aluminum cylinder. The passageway 146 is conformably dimensioned to slidably receive the pin 116. The passageway 146 includes a seal (not shown) or other appropriate means to prevent the fluid contained within the fluid reservoir of the aluminum cylinder from escaping therefrom. Immediately prior to use of the apparatus 10, the source of pressurized fluid is mounted on the adapter assembly 50. More particularly, the threaded stem 145 is screwthreadably mounted on the first threaded end 118 of the adapter main body 115. It should be understood that the pin 116 is operable to puncture the seal as the source of pressurized fluid is mounted on the adaptor main body 115. After the source of pressurized fluid 60 has been mounted on the adapter assembly 50, and after the pin 116 has punctured seal, fluid is permitted to flow from the fluid reservoir of the aluminum cylinder 141 to the third fluid passageway 100. A supplier of the pressurized fluid source 60 is Scott Specialty Gases, Inc., a Scott Medical Products Company of Plumsteadville, Pa.

The infusion cannula 70 includes a distal end 151 and an axially opposed proximal end 152. A conduit (not shown) continuously extends from the distal end 151 to the proximal end 152. Mounted on, or otherwise made integral with, the second end 152 is a female LUER-LOK ® fitting 153. The second fluid filter 42 is removable from the second fluid passageway 99 so that the cannula 70 may be connected to be in fluid communication with the second fluid passageway 99.

The apparatus 10 of the subject invention is used to prepare and administer a fluid mixture in a syringe assembly 20 for injection into body tissue, such as an eye, during a medical procedure. The apparatus 10 is designed to be assembled prior to use in a medical procedure. In this regard, the apparatus 10 is assembled by employing the following steps: the first fluid passageway 98 is connected on the second end 74 of the syringe barrel 71, the first fluid filter 40 is then connected to the third fluid passageway 100, the second fluid filter 42 is next connected to the second fluid passageway 99, the adapter assembly 50 is then connected to the first fluid filter 40, and the source of pressurized fluid 60 is then screwthreadably mounted on the first threaded end 118 of the adapter main body 115 during which the seal is punctured or pierced by the pin 116. The annular handle portion 125 provides a gripping means to securely mount the pressurized source of fluid 60 on the adapter assembly 50.

FIGS. 3 through 5 illustrate the apparatus 10 in a configuration wherein the fluid mixture is prepared within the fluid receiving reservoir of the syringe barrel 71. Fluid from the pressurized source 60 is initially drawn or directed under its own pressure into the fluid receiving reservoir of the syringe barrel 71. To draw up or direct this fluid into the reservoir, the fluid flow director 96 of the regulating means 30 is positioned as illustrated in FIG. 3, such that the indicating lever 97 is positioned in a manner that the second passageway 99 is "OFF." In this arrangement, fluid is permitted to flow into the fluid receiving reservoir of the syringe barrel 71 from the fluid reservoir of the aluminum cylinder 141. In this regard, the fluid flows from the fluid reservoir of the cylinder 141, through the bore 129 and passageway 135 of the pin 116, through the passageway of the adapter assembly 50, through the first filter 40, and through the third fluid passageway 100 and the first fluid passageway 98. To control the flow of fluid into the fluid receiving reservoir of the syringe barrel 71, a user of the apparatus 10 gently pulls back the plunger 72 until a predetermined volume of gas is disposed within the internal reservoir of the syringe barrel 71, as indicated by the volume indicating means 86. The fluid flow director 96 is next positioned in the position as illustrated in FIG. 4, such that the indicating lever 97 is positioned in a manner that the third passageway 100 is "OFF." By positioning the lever 97 such that that third passageway is "OFF," fluid flow is permitted to flow within the three-way stopcock main body 95 between the first fluid passageway 98 and the second fluid passageway 99. In allowing fluid flow between the first and second fluid passageways 98 and 99, the pressure in the fluid receiving reservoir of the syringe barrel 71 will equilibrate with the ambient atmosphere, as the pressure in the fluid receiving reservoir may be greater than the ambient atmosphere because the fluid has been introduced into the barrel 71 under pressure from the vessel 60. Next, ambient air is introduced into the fluid receiving reservoir of the syringe barrel 71 to prepare a fluid mixture, such as a mixture consisting of 40% sulfur hexafluoride gas and 60% ambient air. To cause ambient air to be drawn into the syringe barrel, a user gently pulls back the syringe plunger 72, and draws up a predetermined volume of ambient air, which is filtered by the second filter assembly 42, into the fluid receiving reservoir of the syringe barrel 71. At this point in time, the fluid flow director 96 is rotated to the position as illustrated in FIG. 5, such that the indicating lever 97 is positioned in a manner that the first passageway 98 is "OFF." In this position, the fluid flow director is operable to prevent the fluid mixture of the syringe barrel from escaping therefrom.

After the fluid mixture has been prepared within the fluid receiving reservoir of the syringe barrel 71, the apparatus 10 is then readied for injection into body tissue. At this point in time, the second fluid filter 42 is removed from the second passageway 99, and the infusion cannula 70 is then substituted therefor and connected on the fluid flow regulating means in fluid communication with the second passageway 99, as illustrated in FIG. 1. Just prior to injection, the fluid flow director 96 is then again positioned in a manner that the indicating lever 97 is positioned such that the third passageway 100 is "OFF," and the fluid mixture is injected into body tissue, such as an eye, when the plunger 72 is gently pushed forward toward the second end 74 of the syringe barrel 71.

It is anticipated that the apparatus 10 of the present invention is especially well suited to be manufactured and sold in the form of a sterile kit, which may be assembled at a predetermined time for use during a medical procedure to inject a fluid mixture within body tissue, such as an eye. The kit would be manufactured to be completely disposable after a single use. As earlier discussed hereinabove, the valve 30, the first and second fluid filters 40 and 42, the adapter assembly 50, the source of pressurized fluid 60, and the infusion cannula 70 are all easily, removably connectable in fluid communication one to the other. Therefore, the disposable kit would include, a syringe assembly having a barrel 71 and a plunger 72, a removable cannula 70, a pair of first and second fluid filters 40 and 42, an adapter assembly 50, and a vessel 60.

It is understood that the invention is not confined to the particular construction and arrangement of parts herein illustrated and described, but embraces such modified forms thereof as will come within the scope of the following claims.

What is claimed is:

1. An apparatus for preparing and administering a dose of a fluid mixture for injection into an eye during a medical procedure; the apparatus comprising:

(a) a syringe having a hollow barrel and a plunger which travels within the hollow barrel to regulate fluid flow within, the hollow barrel having a first end and a second end that oppose each other such that travel of the plunger toward the second end forces fluid from the hollow barrel and travel toward the first end draws fluid into the hollow barrel;

(b) a cannula having a proximal end and a distal end, the cannula defining a conduit therethrough which extends from the proximal end to the distal end;

(c) a valve positioned intermediate the syringe and the cannula, the valve having a first passageway connected to be in fluid communication with the hollow barrel, a second passageway connected to be in fluid communication with the proximal end of the cannula, a third passageway connected to receive a first fluid, and a means for selectively directing fluid flow between two of the different passageways, and blocking flow in the remaining passageway, wherein the fluid flow is selectively directed from the third passageway to the hollow barrel to introduce the first fluid to the hollow barrel of the syringe for mixing with a second fluid to form the dose of the fluid mixture, and further wherein the fluid flow is selectively directed from the first passageway to the second passageway to permit fluid flow from the hollow barrel of the syringe to the distal end of the cannula to thereby administer the dose of the fluid into the eye by injection upon travel of the plunger toward the second end of the hollow barrel; and (d) a vessel which is connected to the third passageway, the vessel containing the first fluid under pressure, wherein the second fluid is air which is drawn into the hollow barrel by travel of the plunger toward the first end of the hollow barrel and the first fluid is an inert gas.

2. The apparatus of claim 1 wherein the barrel includes a means for measuring a volume of fluid contained within.

3. The apparatus of claim 1 wherein the cannula is removably connected to the valve and, upon removal of the cannula, the second fluid may be introduced at the second passageway into the hollow barrel of the syringe for mixing with the first fluid upon selectively directing fluid flow from the second passageway to the first passageway by the means for selectively directing fluid flow between the different passageways.

4. The apparatus of claim 3 further including a removable filter located intermediate the cannula and the second passageway, the filter having pores of a size to prevent passage of contaminants or microbes.

5. The apparatus of claim 1 further including a filter located intermediate the vessel and the third passageway, the filter having pores of a size to prevent passage of contaminants or microbes.

6. The apparatus of claim 5 further including an adapter intermediate the filter and the vessel to form a fluid connection therebetween, the adapter including a pin which punctures the vessel upon making the fluid connection to form a hole in the vessel, the hole rendering the vessel unusable for subsequent refilling of the vessel.

7. An apparatus for preparing and administering a dose of fluid mixture for injection into body tissue during a medical procedure, the apparatus comprising:

(a) a syringe having a hollow barrel and a plunger which travels within the hollow barrel to regulate fluid flow within, the hollow barrel having a first end ad a second end that oppose each other such that travel of the plunger toward the second end forces fluid from the hollow barrel and travel toward the first end draws fluid into the hollow barrel;

(b) a cannula having a proximal end and a distal end, the cannula defining a conduit therethrough which extends from the proximal end to the distal end;

(c) a valve positioned intermediate the syringe and the cannula, the valve having a first passageway connected to be in fluid communication with the hollow barrel, a second passageway connected to be in fluid communication with the proximate end of the cannula, a third passageway connected to receive a first fluid, and a means for selectively directing fluid flow between the different passageways, wherein the fluid flow is selectively directed from the third passageway to the hollow barrel to introduce the first fluid to the hollow barrel of the syringe for mixing with a second fluid to form the dose of the fluid mixture, wherein the first fluid is sulfur hexafluoride, and further wherein the fluid flow is selectively directed from the first passageway to the second passageway to permit fluid flow from the hollow barrel of the syringe to the distal end of the cannula to thereby administer the dose of the fluid into the body tissue by injection upon travel of the plunger toward the second end of the hollow barrel; and (d) a vessel which is connected to the third passageway, the vessel containing the first fluid under pressure.

8. An apparatus for preparing and administering a dose of fluid mixture for injection into body tissue during a medical procedure, the apparatus comprising:

(a) a syringe having a hollow barrel and a plunger which travels within the hollow barrel to regulate fluid flow within, the hollow barrel having a first end and a second end that oppose each other such that travel of the plunger toward the second end forces fluid from the hollow barrel and travel toward the first end draws fluid into the hollow barrel;

(b) a cannula having a proximal end and a distal end, the cannula defining a conduit therethrough which extends from the proximal end to the distal end;

(c) A valve positioned intermediate the syringe and the cannula, the valve having a first passageway connected to be in fluid communication with the hollow barrel, a second passageway connected to be in fluid communication with the proximate end of the cannula, a third passageway connected to receive a first fluid, and a means for selectively directing fluid flow between the different passageways, wherein the fluid flow is selectively directed from the third passageway to the hollow barrel to introduce the first fluid to the hollow barrel of the syringe for mixing with a second fluid to form the dose of the fluid mixture, wherein the first fluid is perfluoropropane, and further wherein the fluid flow is selectively directed from the first passageway to the second passageway to permit fluid flow from the hollow barrel of the syringe to the distal end of the cannula to thereby administer the dose of the fluid into the body tissue by injection upon travel of the plunger toward the second end of the hollow barrel; and (d) a vessel which is connected to the third passageway, the vessel containing the first fluid under pressure.

9. An apparatus for preparing and administering a dose of a fluid mixture for injection into an eye during a medical procedure, the apparatus comprising:

(a) a syringe having a hollow barrel and a plunger which travels within the hollow barrel to regulate fluid flow within, the hollow barrel having a first end and a second end that oppose each other such that travel of the plunger toward the second end forces fluid from the hollow barrel, and travel toward the first end draws fluid into the hollow barrel;

(b) a cannula having a proximal end and a distal end, the cannula defining a conduit therethrough which extends from the proximal end to the distal end;

(c) a vessel containing a first fluid under pressure; and (d) a valve positioned intermediate the syringe and the cannula, the valve having a first passageway connected to be in fluid communication with the hollow barrel, a second passageway connected to be in fluid communication to the proximal end of the cannula, a third passageway connected to the vessel containing the first fluid under pressure, and a means for selectively directing fluid flow between two of the different passageways and simultaneously blocking flow to the remaining passageway, wherein the fluid flow is selectively directed from the third passageway to the hollow barrel to introduce the first fluid to the hollow barrel, wherein the fluid flow is selectively directed from the second passageway to the first passageway upon removal of the cannula to introduce the second fluid at the second passageway into the hollow barrel of the syringe for mixing with the first fluid to form the dose of the fluid mixture, and further wherein the fluid flow is selectively directed from the first passageway to the second passageway to permit fluid flow from the hollow barrel of the syringe to the distal end of the cannula and thereby administer the dose of the fluid into the eye by injection upon travel of the plunger toward the second end of the hollow barrel, wherein the second fluid is air which is drawn into the hollow barrel by travel of the plunger toward the first end of the hollow barrel and the first fluid is an inert gas.

10. The apparatus of claim 9 wherein the barrel includes a means for measuring a volume of fluid contained within.

11. The apparatus of claim 9 further including a filter located intermediate the vessel and the third passageway, the filter having pores of a size to prevent passage of contaminants or microbes.

12. The apparatus of claim 11 further including an adapter intermediate the filter and the vessel to form a fluid connection therebetween, the adapter including a pin which punctures the vessel upon making the fluid connection to form a hole in the vessel, the hole rendering the vessel unusable for subsequent refilling of the vessel.

13. The apparatus of claim 9 further including a removable filter located intermediate the cannula and the second passageway, the filter having pores of a size to prevent passage of contaminants or microbes.

14. An apparatus for preparing and administering a dose of fluid mixture for injection into body tissue during a medical procedure, the apparatus comprising:
(a) a syringe having a hollow barrel and a plunger which travels within the hollow barrel to regulate fluid flow within, the hollow barrel having a first end and a second end that oppose each other such that travel of the plunger toward the second end forces fluid from the hollow barrel, and travel toward the first end draws fluid into the hollow barrel;
(b) a cannula having a proximal end and a distal end, the cannula defining a conduit therethrough which extends from the proximal end to the distal end;
(c) a vessel containing a first fluid under pressure; and
(d) a valve positioned intermediate the syringe and the cannula, the valve having a first passageway connected to be in fluid communication with the hollow barrel, a second passageway connected to be in fluid communication to the proximal end of the cannula, a third passageway connected to the vessel containing the first fluid under pressure, and a means for selectively directing fluid flow between the different passageways, wherein the fluid flow is selectively directed from the third passageway to the hollow barrel to introduce the first fluid to the hollow barrel, wherein the fluid flow is selectively directed from the second passageway to the first passageway upon removal of the cannula to introduce a second fluid at the second passageway into the hollow barrel of the syringe for mixing with the first fluid to form the dose of the fluid mixture, wherein the first fluid is sulfur hexafluoride, and further wherein the fluid flow is selectively directed from the first passageway to the second passageway to permit fluid flow from the hollow barrel of the syringe to the distal end of the cannula and thereby administer the dose of the fluid into the body tissue by injection upon travel of the plunger toward the second end of the hollow barrel.

15. An apparatus for preparing and administering a does of fluid mixture for injection into body tissue during a medical procedure, the apparatus comprising:
(a) a syringe having a hollow barrel and a plunger which travels within the hollow barrel to regulate fluid flow within, the hollow barrel having a first end and a second end that oppose each other such that travel of the plunger toward the second end forces fluid from the hollow barrel, and travel toward the first end draws fluid into the hollow barrel;
(b) a cannula having a proximal end and a distal end, the cannula defining a conduit therethrough which extends from the proximal end to the distal end;
(c) a vessel containing a first fluid under pressure; and
(d) a valve positioned intermediate the syringe and the cannula, the valve having a first passageway connected to be in fluid communication with the hollow barrel, a second passageway connected to be in fluid communication to the proximal end of the cannula, a third passageway connected to the vessel containing the first fluid under pressure, and a means for selectively directing fluid flow between the different passageways, wherein the fluid flow is selectively directed from the third passageway to the hollow barrel to introduce the first fluid to the hollow barrel, wherein the fluid flow is selectively directed from the second passageway to the first passageway upon removal of the cannula to introduce a second fluid at the second passageway into the hollow barrel of the syringe for mixing with the first fluid to form the dose of the fluid mixture, wherein the first fluid is perfluoropropane, and further wherein the fluid flow is selectively directed from the first passageway to the second passageway to permit fluid flow from the hollow barrel of the syringe to the distal end of the cannula and thereby administer the dose of the fluid into the body tissue by injection upon travel of the plunger toward the second end of the hollow barrel.

16. An apparatus for preparing and administering a dose of a fluid mixture for injection into an eye during a medical procedure, the apparatus comprising,
(a) a syringe having a hollow barrel and a plunger which travels within the hollow barrel to regulate fluid flow within, the hollow barrel having a first end and a second end that oppose each other such that travel of the plunger toward the second end forces fluid from the hollow barrel and travel toward the first end draws fluid into the hollow barrel, and wherein the barrel includes a means for measuring a volume of fluid contained within;

(b) a cannula having a proximal end and a distal end, the cannula defining a conduit therethrough which extends from the proximal end to the distal end;
(c) a vessel containing a first fluid under pressure;
(d) a valve positioned intermediate the syringe and the cannula, the valve having a first passageway connected to be in fluid communication with the hollow barrel, a second passageway connected to be in fluid communication with the proximal end of the cannula, a third passageway connected to the vessel containing the first fluid under pressure, and a means for selectively directing fluid flow between two of the means for selectively directing fluid flow between two of the different passageways and simultaneously blocking flow to the remaining passageway, wherein the fluid flow is selectively directed from the third passageway to the hollow barrel to introduce the first fluid to the hollow barrel, wherein the fluid flow is selectively directed from the second passageway to the first passageway upon removal of the cannula to introduce the second fluid at the second passageway into the hollow barrel of the syringe for mixing with the first fluid to form the dose of the fluid mixture, and further wherein the fluid flow is selectively directed from the first passageway to the second passageway to permit fluid flow from the hollow barrel of th syringe to the distal end of the cannula and thereby administer the dose of the fluid into the eye by injection upon travel of the plunger toward the second end of the hollow barrel;
(e) a first filter located intermediate the vessel and the third passageway, the filter having pores of a size to prevent passage of contaminants or microbes;
(f) a second filter located intermediate the cannula and the second passageway, the filter having pores of a size to prevent passage of contaminants or microbes; and
(g) an adapter intermediate the first filter and the vessel to form a fluid connection therebetween, the adapter including a pin which punctures the vessel upon making the fluid connection to form a hole in the vessel, the hole rendering the vessel unusable for subsequent refilling of the vessel, wherein the second fluid is air which is drawn into the hollow barrel by travel of the plunger toward the first end of the hollow barrel and the first fluid is an inert gas.

17. A method for preparing and administering a dose of a fluid mixture for injection into an eye by use of a syringe and a cannula, the syringe including a hollow barrel and a plunger which travels within the hollow barrel to regulate fluid flow within, the method comprising the steps of:

(a) directing flow of an inert gas from a pressurized source to the hollow barrel of the syringe;
(b) discontinuing the flow of the inert gas when a predetermined volume of the inert gas fills the hollow barrel;
(c) directing flow of air to the hollow barrel of the syringe to form the fluid mixture;
(d) discontinuing flow of the air when a predetermined volume of the air fills the hollow barrel to form a fluid mixture with desired ratios of the inert gas and air; and
(e) injecting the fluid mixture into the eye.

18. A kit for preparing and administering a dose of a fluid mixture for injection into an eye during a medical procedure, the kit comprising:

(a) a syringe having a hollow barrel and a plunger which travels within the hollow barrel to regulate fluid flow within, the hollow barrel having a first end and a second end that oppose each other such that travel of the plunger toward the second end forces fluid from the hollow barrel and travel toward the first end draws fluid into the hollow barrel;
(b) a cannula having a proximal end and a distal end, the cannula defining a conduit therethrough which extends from the proximal end to the distal end;
(c) a valve positioned intermediate the syringe and the cannula, the valve having a first passageway which is adapted to be connected in fluid communication with the hollow barrel, a second passageway which is adapted to be connected in fluid communication to the proximal end of cannula, a third passageway which is adapted to receive a first fluid, and a means for selectively directing fluid flow between two of the different passageways and simultaneously blocking flow to the remaining passageway, and wherein the fluid flow is selectively directed from the third passageway to the hollow barrel to introduce the first fluid to the hollow barrel of the syringe for mixing with a second fluid to form the dose of the fluid mixture, and further wherein the fluid flow is selectively directed from the first passageway to the second passageway to permit fluid flow from the hollow barrel of the syringe to the distal end of the cannula and thereby administer the dose of the fluid into the eye by injection upon travel of the plunger toward the second end of the hollow barrel; and
(d) a vessel which is connected to the third passageway, the vessel containing the first fluid under pressure, wherein the second fluid is air which is drawn into the hollow barrel by travel of the plunger toward the first end of the hollow barrel and the first fluid is an inert gas.

* * * * *